(12) United States Patent
Arramon

(10) Patent No.: US 9,220,603 B2
(45) Date of Patent: Dec. 29, 2015

(54) LIMITED MOTION PROSTHETIC INTERVERTEBRAL DISC

(75) Inventor: Yves Arramon, Sunnyvale, CA (US)

(73) Assignee: Simplify Medical, Inc., Sunnyvale, CA (US)

( * ) Notice: Subject to any disclaimer, the term of this patent is extended or adjusted under 35 U.S.C. 154(b) by 788 days.

(21) Appl. No.: 12/496,057

(22) Filed: Jul. 1, 2009

(65) Prior Publication Data

US 2010/0004746 A1 Jan. 7, 2010

Related U.S. Application Data

(60) Provisional application No. 61/077,806, filed on Jul. 2, 2008.

(51) Int. Cl.
*A61F 2/44* (2006.01)
*A61F 2/30* (2006.01)

(52) U.S. Cl.
CPC ....... *A61F 2/4425* (2013.01); *A61F 2002/3008* (2013.01); *A61F 2002/30652* (2013.01); *A61F 2002/30655* (2013.01);
(Continued)

(58) Field of Classification Search
CPC .................... A61F 2/4425; A61F 2002/30652; A61F 2002/30655; A61F 2002/30662; A61F 2002/30665; Y10T 403/32647
USPC ............ 623/17.11–17.16, 19.12, 20.2, 20.22, 623/20.26, 21.13, 23.24; 403/113, 114, 121
See application file for complete search history.

(56) References Cited

U.S. PATENT DOCUMENTS 3,486,505 A   12/1969 Morrison
3,867,728 A    2/1975 Stubstad et al.
(Continued)

FOREIGN PATENT DOCUMENTS

| DE | 3023353 A1 | 4/1981 |
|----|------------|--------|
| EP | 0 333 990 A2 | 9/1989 |
| EP | 0 560 140 A1 | 9/1993 |
| EP | 0 560 141 A1 | 9/1993 |
| EP | 0 591 712 A1 | 4/1994 |
| EP | 0 820 740 | 1/1998 |
| EP | 1 142 544 A1 | 10/2001 |
| EP | 1 153 582 A2 | 11/2001 |
| EP | 1 250 898 A1 | 10/2002 |
| EP | 1293180 A1 | 3/2003 |

(Continued)

OTHER PUBLICATIONS

Buttner-Janz, "The Development of the Artificial Disc," Introduction, pp. 1-18, Library of Congress Catalogue No. 92-75582, ISBN 0-9635430-0-8 (1989).

(Continued)

*Primary Examiner* — Jan Christopher Merene
*Assistant Examiner* — Atiya Mahmud
(74) *Attorney, Agent, or Firm* — Wilson, Sonsini, Goodrich & Rosati

(57) ABSTRACT

A prosthetic intervertebral disc includes an upper plate and a lower plate and employs congruent stepped features to provide limited articulating motion between the plates. The stepped features can be used to provide articulating motion of a rocking type rather than a rubbing or translating type of motion provided in many artificial discs. Each of two parts of the intervertebral disc includes two or more stepped bearing surfaces, having curved or flat shapes, which mate with one another to provide the articulation to the disc. The stepped features can be designed to restrict motion in flexion-extension or lateral bending to less than a predetermined angle. The stepped design can be modified to either allow or prevent rotational motion between the plates. The limited motion disc substantially prevents translation, however some limited translation can be provided by modification of the relative sizes of the stepped features.

14 Claims, 7 Drawing Sheets

(52) U.S. Cl.
CPC .......... *A61F 2002/30662* (2013.01); *A61F 2002/30665* (2013.01); *A61F 2002/30843* (2013.01); *A61F 2002/30884* (2013.01); *A61F 2002/30899* (2013.01); *A61F 2250/0098* (2013.01); *A61F 2310/00017* (2013.01); *A61F 2310/00023* (2013.01); *A61F 2310/0088* (2013.01); *A61F 2310/00407* (2013.01); *A61F 2310/00796* (2013.01)

(56) References Cited

U.S. PATENT DOCUMENTS

| | | |
|---|---|---|
| 4,309,777 A | 1/1982 | Patil |
| 4,531,917 A | 7/1985 | Linkow et al. |
| 4,566,466 A | 1/1986 | Ripple et al. |
| 4,619,660 A | 10/1986 | Christiansen et al. |
| 4,673,407 A | 6/1987 | Martin |
| 4,759,766 A | 7/1988 | Buttner-Janz et al. |
| 4,759,769 A | 7/1988 | Hedman et al. |
| 4,834,757 A | 5/1989 | Brantigan |
| 4,863,477 A | 9/1989 | Monson |
| 4,904,261 A | 2/1990 | Dove et al. |
| 4,917,704 A | 4/1990 | Frey et al. |
| 4,932,969 A | 6/1990 | Frey et al. |
| 4,946,378 A | 8/1990 | Hirayama et al. |
| 4,997,432 A | 3/1991 | Keller |
| 5,035,716 A | 7/1991 | Downey |
| 5,057,108 A | 10/1991 | Shetty et al. |
| 5,071,437 A | 12/1991 | Steffee |
| 5,122,130 A | 6/1992 | Keller |
| 5,195,526 A | 3/1993 | Michelson |
| 5,258,031 A | 11/1993 | Salib et al. |
| 5,282,861 A | 2/1994 | Kaplan |
| 5,314,477 A | 5/1994 | Marnay |
| 5,320,644 A | 6/1994 | Baumgartner |
| 5,370,697 A | 12/1994 | Baumgartner |
| 5,394,457 A | 2/1995 | Leibinger et al. |
| 5,401,269 A | 3/1995 | Buttner-Janz et al. |
| 5,415,704 A | 5/1995 | Davidson |
| 5,458,642 A | 10/1995 | Beer et al. |
| 5,462,575 A | 10/1995 | Del Corso |
| 5,484,437 A | 1/1996 | Michelson |
| 5,489,307 A | 2/1996 | Kuslich et al. |
| 5,505,732 A | 4/1996 | Michelson |
| 5,507,816 A | 4/1996 | Bullivant |
| 5,534,030 A | 7/1996 | Navarro et al. |
| 5,556,431 A | 9/1996 | Buttner-Janz |
| 5,674,296 A | 10/1997 | Bryan et al. |
| 5,676,701 A | 10/1997 | Yuan et al. |
| 5,676,702 A | 10/1997 | Ratron |
| 5,683,465 A | 11/1997 | Shinn et al. |
| 5,702,450 A | 12/1997 | Bisserie |
| 5,709,683 A | 1/1998 | Bagby |
| 5,728,159 A | 3/1998 | Stroever et al. |
| 5,741,253 A | 4/1998 | Michelson |
| 5,776,198 A | 7/1998 | Rabbe et al. |
| 5,782,832 A | 7/1998 | Larsen et al. |
| 5,797,909 A | 8/1998 | Michelson |
| 5,824,094 A | 10/1998 | Serhan et al. |
| 5,865,846 A | 2/1999 | Bryan et al. |
| 5,865,848 A | 2/1999 | Baker |
| 5,888,226 A | 3/1999 | Rogozinski |
| 5,895,428 A | 4/1999 | Berry |
| 5,899,901 A | 5/1999 | Middleton |
| 5,899,911 A | 5/1999 | Carter |
| 5,928,284 A | 7/1999 | Mehdizadeh |
| 5,989,251 A | 11/1999 | Nichols |
| 5,989,291 A | 11/1999 | Ralph et al. |
| 6,001,130 A | 12/1999 | Bryan et al. |
| 6,019,792 A | 2/2000 | Cauthen |
| 6,022,376 A | 2/2000 | Assell et al. |
| 6,039,761 A | 3/2000 | Li et al. |
| 6,039,763 A | 3/2000 | Shelokov |
| 6,080,155 A | 6/2000 | Michelson |
| 6,083,228 A | 7/2000 | Michelson |
| 6,086,613 A | 7/2000 | Camino et al. |
| 6,096,038 A | 8/2000 | Michelson |
| 6,132,465 A | 10/2000 | Ray et al. |
| 6,136,031 A | 10/2000 | Middleton |
| 6,139,551 A | 10/2000 | Michelson et al. |
| 6,139,579 A | 10/2000 | Steffee et al. |
| 6,143,033 A | 11/2000 | Paul et al. |
| 6,146,421 A | 11/2000 | Gordon et al. |
| 6,156,067 A | 12/2000 | Bryan et al. |
| 6,159,214 A | 12/2000 | Michelson |
| 6,162,252 A | 12/2000 | Kuras et al. |
| 6,174,311 B1 | 1/2001 | Branch et al. |
| 6,176,881 B1 | 1/2001 | Schar et al. |
| 6,193,757 B1 | 2/2001 | Foley et al. |
| 6,224,595 B1 | 5/2001 | Michelson |
| 6,224,607 B1 | 5/2001 | Michelson |
| 6,231,609 B1 | 5/2001 | Mehdizadeh |
| 6,235,030 B1 | 5/2001 | Zuckerman et al. |
| 6,261,296 B1 | 7/2001 | Aebi et al. |
| 6,264,695 B1 | 7/2001 | Stoy |
| 6,290,726 B1 | 9/2001 | Pope et al. |
| 6,296,664 B1 | 10/2001 | Middleton |
| 6,315,797 B1 | 11/2001 | Middleton |
| 6,322,567 B1 | 11/2001 | Mittelstadt et al. |
| 6,336,941 B1 | 1/2002 | Subba Rao et al. |
| 6,348,071 B1 | 2/2002 | Steffee et al. |
| 6,368,350 B1 | 4/2002 | Erickson et al. |
| 6,368,351 B1 | 4/2002 | Glenn et al. |
| 6,375,681 B1 | 4/2002 | Truscott |
| 6,375,682 B1 | 4/2002 | Fleischmann et al. |
| 6,395,032 B1 | 5/2002 | Gauchet |
| 6,402,785 B1 | 6/2002 | Zdeblick et al. |
| 6,409,766 B1 | 6/2002 | Brett |
| 6,413,278 B1 | 7/2002 | Marchosky |
| 6,416,551 B1 | 7/2002 | Keller |
| 6,436,098 B1 | 8/2002 | Michelson |
| 6,440,139 B2 | 8/2002 | Michelson |
| 6,447,544 B1 | 9/2002 | Michelson |
| 6,475,243 B1 * | 11/2002 | Sheldon et al. ............ 623/22.28 |
| 6,478,800 B1 | 11/2002 | Fraser et al. |
| 6,517,544 B1 | 2/2003 | Michelson |
| 6,517,580 B1 | 2/2003 | Ramadan et al. |
| 6,520,967 B1 | 2/2003 | Cauthen |
| 6,520,996 B1 | 2/2003 | Manasas et al. |
| 6,527,804 B1 | 3/2003 | Gauchet et al. |
| 6,533,817 B1 | 3/2003 | Norton et al. |
| 6,537,279 B1 | 3/2003 | Michelson |
| 6,554,863 B2 | 4/2003 | Paul et al. |
| 6,562,047 B2 | 5/2003 | Ralph et al. |
| 6,562,074 B2 | 5/2003 | Gerbec et al. |
| 6,565,574 B2 | 5/2003 | Michelson |
| 6,579,321 B1 * | 6/2003 | Gordon et al. ............ 623/17.16 |
| 6,582,466 B1 | 6/2003 | Gauchet |
| 6,582,468 B1 | 6/2003 | Gauchet |
| 6,592,624 B1 | 7/2003 | Fraser et al. |
| 6,599,294 B2 | 7/2003 | Fuss et al. |
| 6,607,558 B2 | 8/2003 | Karus |
| 6,607,559 B2 | 8/2003 | Ralph et al. |
| 6,610,092 B2 | 8/2003 | Ralph et al. |
| 6,623,525 B2 | 9/2003 | Ralph et al. |
| 6,645,248 B2 | 11/2003 | Casutt |
| 6,648,895 B2 | 11/2003 | Burkus et al. |
| 6,652,533 B2 | 11/2003 | O'Neil |
| 6,660,038 B2 | 12/2003 | Boyer, II et al. |
| 6,660,040 B2 * | 12/2003 | Chan et al. ................ 623/22.21 |
| 6,666,866 B2 | 12/2003 | Mertz et al. |
| 6,669,731 B2 | 12/2003 | Ralph et al. |
| 6,669,732 B2 | 12/2003 | Serhan et al. |
| 6,673,113 B2 | 1/2004 | Ralph et al. |
| 6,682,562 B2 | 1/2004 | Viart et al. |
| 6,689,132 B2 | 2/2004 | Biscup |
| 6,706,068 B2 | 3/2004 | Ferree |
| 6,709,439 B2 | 3/2004 | Rogers et al. |
| 6,712,819 B2 | 3/2004 | Zucherman et al. |
| 6,712,825 B2 | 3/2004 | Aebi et al. |
| 6,723,097 B2 | 4/2004 | Fraser et al. |
| 6,726,720 B2 | 4/2004 | Ross et al. |
| 6,726,721 B2 | 4/2004 | Stoy et al. |
| 6,733,532 B1 | 5/2004 | Gauchet et al. |

(56) References Cited

U.S. PATENT DOCUMENTS

| | | |
|---|---|---|
| 6,740,118 B2 | 5/2004 | Eisermann et al. |
| 6,740,119 B2 | 5/2004 | Ralph et al. |
| 6,755,841 B2 | 6/2004 | Fraser et al. |
| 6,764,515 B2 | 7/2004 | Ralph et al. |
| 6,770,095 B2 | 8/2004 | Grinberg et al. |
| 6,790,233 B2 | 9/2004 | Brodke et al. |
| 6,793,678 B2 | 9/2004 | Hawkins |
| 6,814,737 B2 | 11/2004 | Cauthen |
| 6,821,298 B1 | 11/2004 | Jackson |
| 6,827,740 B1 | 12/2004 | Michelson |
| 6,846,328 B2 | 1/2005 | Cauthen |
| 6,863,673 B2 | 3/2005 | Gerbec et al. |
| 6,875,213 B2 | 4/2005 | Michelson |
| 6,896,680 B2 | 5/2005 | Michelson |
| 6,899,735 B2 | 5/2005 | Coates et al. |
| 6,936,071 B1 | 8/2005 | Marnay et al. |
| 6,936,132 B2 | 8/2005 | Topolnitsky |
| 6,964,686 B2 | 11/2005 | Gordon |
| 6,966,929 B2 | 11/2005 | Mitchell |
| 6,989,011 B2 | 1/2006 | Paul et al. |
| 6,994,727 B2 | 2/2006 | Khandkar et al. |
| 7,011,684 B2 | 3/2006 | Eckman |
| 7,022,138 B2 | 4/2006 | Mashburn |
| 7,025,787 B2 | 4/2006 | Bryan et al. |
| 7,044,983 B1 | 5/2006 | Cheng |
| 7,056,344 B2 | 6/2006 | Huppert et al. |
| 7,060,073 B2 | 6/2006 | Frey et al. |
| 7,066,958 B2 | 6/2006 | Ferree |
| 7,081,120 B2 | 7/2006 | Li et al. |
| 7,083,651 B2 | 8/2006 | Diaz et al. |
| 7,087,055 B2 | 8/2006 | Lim et al. |
| 7,097,648 B1 | 8/2006 | Globerman et al. |
| 7,115,132 B2 | 10/2006 | Errico et al. |
| 7,118,580 B1 | 10/2006 | Beyersdorff et al. |
| 7,147,665 B1 | 12/2006 | Bryan et al. |
| 7,153,325 B2 | 12/2006 | Kim et al. |
| 7,179,294 B2 | 2/2007 | Eisermann et al. |
| 7,182,784 B2 | 2/2007 | Evans et al. |
| 7,198,644 B2 | 4/2007 | Schultz et al. |
| 7,207,991 B2 | 4/2007 | Michelson |
| 7,214,244 B2 | 5/2007 | Zubok et al. |
| 7,217,291 B2 | 5/2007 | Zucherman et al. |
| 7,235,082 B2 | 6/2007 | Bartish et al. |
| 7,235,103 B2 | 6/2007 | Rivin |
| 7,250,060 B2 | 7/2007 | Trieu |
| 7,255,714 B2 | 8/2007 | Malek |
| 7,261,739 B2 | 8/2007 | Ralph et al. |
| 7,267,688 B2 | 9/2007 | Ferree |
| 7,270,679 B2 | 9/2007 | Istephanous et al. |
| 7,270,682 B2 | 9/2007 | Frigg et al. |
| 7,303,583 B1 | 12/2007 | Schar et al. |
| 7,318,839 B2 | 1/2008 | Malberg et al. |
| 7,326,250 B2 | 2/2008 | Beaurain et al. |
| 7,331,995 B2 | 2/2008 | Eisermann et al. |
| 7,429,270 B2 | 9/2008 | Baumgartner et al. |
| 7,442,211 B2 | 10/2008 | de Villiers et al. |
| 7,452,380 B2 | 11/2008 | Zubok et al. |
| 7,491,241 B2 | 2/2009 | Errico et al. |
| 7,494,508 B2 | 2/2009 | Zeegers |
| 7,531,001 B2 | 5/2009 | de Villiers et al. |
| 8,016,886 B2* | 9/2011 | Albert et al. ............... 623/17.11 |
| 2001/0016773 A1 | 8/2001 | Serhan et al. |
| 2001/0029377 A1 | 10/2001 | Aebi et al. |
| 2002/0022845 A1 | 2/2002 | Zdeblick et al. |
| 2002/0035400 A1 | 3/2002 | Bryan et al. |
| 2002/0045904 A1 | 4/2002 | Fuss et al. |
| 2002/0068936 A1 | 6/2002 | Burkus et al. |
| 2002/0091392 A1 | 7/2002 | Michelson |
| 2002/0116009 A1 | 8/2002 | Fraser et al. |
| 2002/0123753 A1 | 9/2002 | Michelson |
| 2002/0128715 A1 | 9/2002 | Bryan et al. |
| 2002/0165550 A1 | 11/2002 | Frey et al. |
| 2002/0177897 A1 | 11/2002 | Michelson |
| 2002/0198532 A1 | 12/2002 | Michelson |
| 2003/0009224 A1 | 1/2003 | Kuras |
| 2003/0023245 A1 | 1/2003 | Ralph et al. |
| 2003/0028249 A1 | 2/2003 | Baccelli et al. |
| 2003/0040746 A1 | 2/2003 | Mitchell et al. |
| 2003/0045884 A1 | 3/2003 | Robie et al. |
| 2003/0045939 A1 | 3/2003 | Casutt |
| 2003/0074076 A1 | 4/2003 | Ferree |
| 2003/0083747 A1 | 5/2003 | Winterbottom et al. |
| 2003/0100951 A1 | 5/2003 | Serhan et al. |
| 2003/0125739 A1 | 7/2003 | Bagga |
| 2003/0130662 A1 | 7/2003 | Michelson |
| 2003/0135277 A1 | 7/2003 | Bryan et al. |
| 2003/0139812 A1 | 7/2003 | Garcia et al. |
| 2003/0187448 A1 | 10/2003 | Michelson |
| 2003/0191533 A1* | 10/2003 | Dixon et al. ............... 623/17.14 |
| 2003/0191536 A1 | 10/2003 | Ferree |
| 2003/0195517 A1 | 10/2003 | Michelson |
| 2003/0195631 A1 | 10/2003 | Ferree |
| 2003/0199982 A1 | 10/2003 | Bryan |
| 2003/0204261 A1 | 10/2003 | Eisermann et al. |
| 2003/0208271 A1 | 11/2003 | Kuras |
| 2003/0229358 A1 | 12/2003 | Errico et al. |
| 2003/0233145 A1 | 12/2003 | Landry et al. |
| 2004/0002761 A1 | 1/2004 | Rogers et al. |
| 2004/0024407 A1 | 2/2004 | Ralph |
| 2004/0024410 A1 | 2/2004 | Olson et al. |
| 2004/0030391 A1 | 2/2004 | Ferree |
| 2004/0034426 A1 | 2/2004 | Errico et al. |
| 2004/0054411 A1 | 3/2004 | Kelly et al. |
| 2004/0059318 A1 | 3/2004 | Zhang et al. |
| 2004/0073307 A1 | 4/2004 | Keller |
| 2004/0073311 A1 | 4/2004 | Ferree |
| 2004/0073312 A1 | 4/2004 | Eisermann et al. |
| 2004/0093087 A1 | 5/2004 | Ferree et al. |
| 2004/0097928 A1 | 5/2004 | Zdeblick et al. |
| 2004/0098131 A1 | 5/2004 | Bryan et al. |
| 2004/0117021 A1 | 6/2004 | Biedermann et al. |
| 2004/0143270 A1 | 7/2004 | Zucherman et al. |
| 2004/0143332 A1 | 7/2004 | Krueger et al. |
| 2004/0143334 A1 | 7/2004 | Ferree |
| 2004/0167626 A1 | 8/2004 | Geremakis et al. |
| 2004/0176843 A1 | 9/2004 | Zubok et al. |
| 2004/0186569 A1 | 9/2004 | Berry |
| 2004/0215342 A1 | 10/2004 | Suddaby |
| 2004/0225295 A1 | 11/2004 | Zubok et al. |
| 2004/0225365 A1 | 11/2004 | Eisermann et al. |
| 2004/0236426 A1 | 11/2004 | Ralph et al. |
| 2004/0254644 A1 | 12/2004 | Taylor |
| 2005/0015094 A1 | 1/2005 | Keller |
| 2005/0015095 A1 | 1/2005 | Keller |
| 2005/0015152 A1 | 1/2005 | Sweeney |
| 2005/0021145 A1 | 1/2005 | de Villiers et al. |
| 2005/0021146 A1 | 1/2005 | de Villiers et al. |
| 2005/0027360 A1 | 2/2005 | Webb et al. |
| 2005/0038515 A1 | 2/2005 | Kunzler |
| 2005/0043800 A1 | 2/2005 | Paul et al. |
| 2005/0085917 A1 | 4/2005 | Marnay et al. |
| 2005/0107881 A1 | 5/2005 | Alleyne et al. |
| 2005/0113842 A1 | 5/2005 | Bertagnoli et al. |
| 2005/0113928 A1 | 5/2005 | Cragg |
| 2005/0143824 A1 | 6/2005 | Richelsoph et al. |
| 2005/0149189 A1 | 7/2005 | Mokhtar et al. |
| 2005/0154462 A1* | 7/2005 | Zucherman et al. ....... 623/17.15 |
| 2005/0154463 A1 | 7/2005 | Trieu |
| 2005/0165408 A1 | 7/2005 | Puno et al. |
| 2005/0192586 A1 | 9/2005 | Zuckerman et al. |
| 2005/0192670 A1 | 9/2005 | Zubok et al. |
| 2005/0197706 A1 | 9/2005 | Hovorka et al. |
| 2005/0216081 A1 | 9/2005 | Taylor |
| 2005/0216084 A1 | 9/2005 | Fleischmann et al. |
| 2005/0216092 A1* | 9/2005 | Marik et al. ............... 623/23.39 |
| 2005/0234553 A1 | 10/2005 | Gordon |
| 2005/0251260 A1 | 11/2005 | Gerber et al. |
| 2005/0251261 A1 | 11/2005 | Peterman |
| 2005/0261772 A1 | 11/2005 | Filippi et al. |
| 2005/0267580 A1 | 12/2005 | Suddaby |
| 2005/0267581 A1 | 12/2005 | Marnay et al. |
| 2006/0004377 A1 | 1/2006 | Keller |
| 2006/0004453 A1 | 1/2006 | Bartish et al. |
| 2006/0015183 A1 | 1/2006 | Gilbert et al. |

(56) References Cited

U.S. PATENT DOCUMENTS

| | | |
|---|---|---|
| 2006/0020342 A1 | 1/2006 | Ferree et al. |
| 2006/0020344 A1* | 1/2006 | Shultz et al. ............... 623/19.12 |
| 2006/0025862 A1 | 2/2006 | de Villiers et al. |
| 2006/0029186 A1 | 2/2006 | de Villiers et al. |
| 2006/0030857 A1 | 2/2006 | de Villiers et al. |
| 2006/0030862 A1 | 2/2006 | de Villiers et al. |
| 2006/0036325 A1* | 2/2006 | Paul et al. ................... 623/17.14 |
| 2006/0036327 A1* | 2/2006 | Enayati ....................... 623/17.15 |
| 2006/0041313 A1 | 2/2006 | Allard et al. |
| 2006/0041314 A1 | 2/2006 | Millard |
| 2006/0052870 A1 | 3/2006 | Feree |
| 2006/0069439 A1* | 3/2006 | Zucherman et al. ........ 623/17.14 |
| 2006/0142858 A1 | 6/2006 | Colleran |
| 2006/0142862 A1 | 6/2006 | Diaz et al. |
| 2006/0155378 A1 | 7/2006 | Eckman |
| 2006/0167549 A1 | 7/2006 | Mathys et al. |
| 2006/0178744 A1 | 8/2006 | de Villiers et al. |
| 2006/0178746 A1 | 8/2006 | Bartish, Jr. et al. |
| 2006/0195097 A1 | 8/2006 | Evans et al. |
| 2006/0200239 A1 | 9/2006 | Rothman et al. |
| 2006/0224241 A1 | 10/2006 | Butler et al. |
| 2006/0235426 A1 | 10/2006 | Lim et al. |
| 2006/0235525 A1 | 10/2006 | Gil et al. |
| 2006/0235527 A1 | 10/2006 | Buettner-Janz et al. |
| 2006/0241641 A1 | 10/2006 | Albans et al. |
| 2006/0241766 A1 | 10/2006 | Felton et al. |
| 2006/0259144 A1 | 11/2006 | Trieu |
| 2006/0259146 A1 | 11/2006 | Navarro et al. |
| 2006/0265068 A1 | 11/2006 | Schwab |
| 2006/0293752 A1 | 12/2006 | Moumene et al. |
| 2006/0293754 A1 | 12/2006 | de Villiers et al. |
| 2007/0010826 A1 | 1/2007 | Rhoda et al. |
| 2007/0021837 A1 | 1/2007 | Ashman et al. |
| 2007/0032875 A1 | 2/2007 | Blacklock et al. |
| 2007/0055378 A1* | 3/2007 | Ankney et al. .............. 623/17.15 |
| 2007/0061011 A1 | 3/2007 | de Villiers et al. |
| 2007/0067035 A1 | 3/2007 | Falahee |
| 2007/0067036 A1 | 3/2007 | Hudgins et al. |
| 2007/0073398 A1 | 3/2007 | Fabian et al. |
| 2007/0088442 A1* | 4/2007 | Cima et al. .................. 623/18.11 |
| 2007/0093898 A1 | 4/2007 | Schwab et al. |
| 2007/0100453 A1 | 5/2007 | Parsons et al. |
| 2007/0100454 A1 | 5/2007 | Burgess et al. |
| 2007/0100456 A1 | 5/2007 | Dooris et al. |
| 2007/0123903 A1 | 5/2007 | Raymond et al. |
| 2007/0123904 A1 | 5/2007 | Stad et al. |
| 2007/0135923 A1 | 6/2007 | Peterman et al. |
| 2007/0162133 A1* | 7/2007 | Doubler et al. ............. 623/17.11 |
| 2007/0168033 A1 | 7/2007 | Kim et al. |
| 2007/0168036 A1 | 7/2007 | Ainsworth et al. |
| 2007/0179615 A1 | 8/2007 | Heinz et al. |
| 2007/0191958 A1* | 8/2007 | Abdou ......................... 623/17.16 |
| 2007/0213821 A1 | 9/2007 | Kwak et al. |
| 2007/0233077 A1 | 10/2007 | Khalili |
| 2007/0233247 A1 | 10/2007 | Schwab |
| 2007/0233248 A1 | 10/2007 | Schwab et al. |
| 2007/0233251 A1 | 10/2007 | Abdou |
| 2007/0270970 A1 | 11/2007 | Trieu |
| 2007/0282449 A1 | 12/2007 | de Villiers et al. |
| 2007/0299521 A1 | 12/2007 | Glenn et al. |
| 2008/0015698 A1 | 1/2008 | Marino et al. |
| 2008/0015701 A1 | 1/2008 | Garcia et al. |
| 2008/0021557 A1 | 1/2008 | Trieu |
| 2008/0051900 A1* | 2/2008 | de Villiers et al. ......... 623/17.16 |
| 2008/0051901 A1* | 2/2008 | de Villiers et al. ......... 623/17.16 |
| 2008/0058930 A1* | 3/2008 | Edie et al. ................... 623/17.11 |
| 2008/0077243 A1* | 3/2008 | Lee et al. .................... 623/17.15 |
| 2008/0103601 A1 | 5/2008 | Biro et al. |
| 2008/0119932 A1* | 5/2008 | Lechmann et al. ......... 623/17.11 |
| 2008/0125864 A1 | 5/2008 | de Villiers et al. |
| 2008/0133011 A1 | 6/2008 | de Villiers et al. |
| 2008/0154301 A1 | 6/2008 | de Villiers et al. |
| 2008/0154382 A1 | 6/2008 | de Villiers et al. |
| 2008/0195212 A1* | 8/2008 | Nguyen et al. .............. 623/17.16 |
| 2008/0215155 A1 | 9/2008 | de Villiers et al. |
| 2008/0221696 A1 | 9/2008 | de Villiers et al. |
| 2008/0228274 A1 | 9/2008 | de Villiers et al. |
| 2008/0228277 A1 | 9/2008 | de Villiers et al. |
| 2008/0228281 A1* | 9/2008 | Forrer et al. ................ 623/19.12 |
| 2008/0294259 A1 | 11/2008 | de Villiers et al. |
| 2009/0043391 A1 | 2/2009 | de Villiers et al. |
| 2009/0048674 A1 | 2/2009 | Zubok et al. |
| 2009/0048677 A1 | 2/2009 | McLeod et al. |
| 2009/0076614 A1 | 3/2009 | Arramon |
| 2009/0105833 A1 | 4/2009 | Hovda et al. |
| 2009/0105834 A1 | 4/2009 | Hovda et al. |
| 2009/0105835 A1 | 4/2009 | Hovda et al. |
| 2009/0222101 A1 | 9/2009 | de Villiers et al. |
| 2009/0276051 A1 | 11/2009 | Arramon et al. |
| 2010/0016972 A1 | 1/2010 | Jansen et al. |
| 2010/0016973 A1 | 1/2010 | de Villiers et al. |
| 2010/0286784 A1* | 11/2010 | Curran et al. ............... 623/17.16 |

FOREIGN PATENT DOCUMENTS

| | | |
|---|---|---|
| EP | 1 306 064 A1 | 5/2003 |
| EP | 1321113 A2 | 6/2003 |
| EP | 1 344 493 A1 | 9/2003 |
| EP | 1 344 506 A1 | 9/2003 |
| EP | 1 344 507 A2 | 9/2003 |
| EP | 1 344 508 A3 | 9/2003 |
| EP | 1 405 615 A1 | 4/2004 |
| EP | 1 417 940 A1 | 5/2004 |
| EP | 1 570 813 | 9/2005 |
| FR | 2 803 741 | 7/2001 |
| JP | 61-122859 | 6/1986 |
| JP | 63-164948 | 7/1988 |
| JP | 01-136655 | 5/1989 |
| JP | 06-007391 | 1/1994 |
| JP | 2002-521090 T | 7/2002 |
| JP | 2003-508119 T | 3/2003 |
| WO | WO 99/20209 | 4/1999 |
| WO | WO 99/30651 | 6/1999 |
| WO | WO 00/04851 | 2/2000 |
| WO | WO 00/35384 | 6/2000 |
| WO | WO 00/42954 | 7/2000 |
| WO | WO 01/01893 A1 | 1/2001 |
| WO | WO 01/15637 | 3/2001 |
| WO | WO 01/68003 A1 | 9/2001 |
| WO | WO 02/11650 | 2/2002 |
| WO | WO 04/000170 | 12/2003 |
| WO | WO 04/000171 | 12/2003 |
| WO | WO 2004/026187 A1 | 4/2004 |
| WO | WO 2004/054477 | 7/2004 |
| WO | WO 2005/004756 A2 | 1/2005 |
| WO | WO 2005/004756 A3 | 1/2005 |
| WO | WO 2005/053580 A1 | 6/2005 |
| WO | WO 2005/072662 | 8/2005 |
| WO | WO 2005/112834 | 12/2005 |
| WO | WO 2006/119092 A2 | 11/2006 |
| WO | WO 2006/119092 A3 | 11/2006 |
| WO | WO 2007/121320 | 10/2007 |
| ZA | 03/9312 | 11/2003 |

OTHER PUBLICATIONS

Hellier et al., "Wear Studies for Development of an Intervertebral Disc Prosthesis," *Spine*, vol. 17 No. 6 Supplement pp. 86-96 (1992).

Lee et al., "Impact Response of the Intervertebral Disc in a Finite-Element Model," *Spine* vol. 25, No. 19, pp. 2431-2439 (2000).

Lehuec et al., "Shock Absorption in Lumber Disc Prosthesis," *Journal of Spinal Disorders & Techniques*, vol. 16, No. 4, pp. 346-351(2003).

International Search Report and Written Opinion of PCT Application No. PCT/US2009/049619, mailed Jan. 25, 2010, 10 pages total.

European search report and opinion dated Aug. 13, 2013 for EP Application No. 09774568.1.

\* cited by examiner

LIMITED MOTION PROSTHETIC INTERVERTEBRAL DISC

CROSS-REFERENCES TO RELATED APPLICATIONS

This application claims priority to U.S. Provisional Application No. 61/077,806, filed Jul. 2, 2008, entitled "LIMITED MOTION PROSTHETIC INTERVERTEBRAL DISC," the full disclosure of which is incorporated herein by reference.

BACKGROUND OF THE INVENTION

The present invention relates to medical devices and methods. More specifically, the invention relates to intervertebral prosthetic discs and methods of preserving limited motion upon removal of an intervertebral disc.

Back pain takes an enormous toll on the health and productivity of people around the world. According to the American Academy of Orthopedic Surgeons, approximately 80 percent of Americans will experience back pain at some time in their life. In the year 2000, approximately 26 million visits were made to physicians' offices due to back problems in the United States. On any one day, it is estimated that 5% of the working population in America is disabled by back pain.

One common cause of back pain is injury, degeneration and/or dysfunction of one or more intervertebral discs. Intervertebral discs are the soft tissue structures located between each of the thirty-three vertebral bones that make up the vertebral (spinal) column. Essentially, the discs allow the vertebrae to move relative to one another. The vertebral column and discs are vital anatomical structures, in that they form a central axis that supports the head and torso, allow for movement of the back, and protect the spinal cord, which passes through the vertebrae in proximity to the discs.

Discs often become damaged due to wear and tear or acute injury. For example, discs may bulge (herniate), tear, rupture, degenerate or the like. A bulging disc may press against the spinal cord or a nerve exiting the spinal cord, causing "radicular" pain (pain in one or more extremities caused by impingement of a nerve root). Degeneration or other damage to a disc may cause a loss of "disc height," meaning that the natural space between two vertebrae decreases. Decreased disc height may cause a disc to bulge, facet loads to increase, two vertebrae to rub together in an unnatural way and/or increased pressure on certain parts of the vertebrae and/or nerve roots, thus causing pain. In general, chronic and acute damage to intervertebral discs is a common source of back related pain and loss of mobility.

When one or more damaged intervertebral discs cause a patient pain and discomfort, surgery is often required. Traditionally, surgical procedures for treating intervertebral discs have involved discectomy (partial or total removal of a disc), with or without interbody fusion of the two vertebrae adjacent to the disc. When the disc is partially or completely removed, it is necessary to replace the excised disc material with natural bone or artificial support structures to prevent direct contact between hard bony surfaces of adjacent vertebrae. Oftentimes, pins, rods, screws, cages and/or the like are inserted between the vertebrae to act as support structures to hold the vertebrae and any graft material in place while the bones permanently fuse together. One typical fusion procedure involves inserting a "cage" between the vertebrae to maintains the space usually occupied by the disc and prevent the vertebrae from collapsing and impinging the nerve roots. The cage is used in combination with bone graft material (either autograft or allograft) such that the two vertebrae and the graft material will grow together over time forming bridging bone between the two vertebrae. The fusion process of growing bridging bone between the vertebrae typically takes 6-12 months after surgery. During in this time external bracing (orthotics) may be required. External factors such as smoking, osteoporosis, certain medications, and heavy activity can prolong or even prevent the fusion process. If fusion does not occur, patients may require reoperation.

A more recent alternative to traditional fusion is total disc replacement or TDR. TDR provides the ability to treat disc related pain without fusion provided by bridging bone, by using a movable, implantable, artificial intervertebral disc (or "disc prosthesis") between two vertebrae. A number of different artificial intervertebral discs are currently being developed. For example, U.S. Patent Application Publication Nos. 2005/0021146, 2005/0021145, and 2006/0025862, which are hereby incorporated by reference in their entirety, describe artificial intervertebral discs with mobile bearing designs. Other examples of intervertebral disc prostheses are the LINK® SB Charité disc (provided by DePuy Spine, Inc.) MOBIDISC® (provided by LDR Medical (www.ldrmedical.fr)), the BRYAN Cervical Disc (provided by Medtronic Sofamor Danek, Inc.), the PRODISC® or PRODISC-C® (from Synthes Stratec, Inc.), the PCM disc (provided by Cervitech, Inc.), and the MAVERICK® disc (provided by Medtronic Sofomor Danek). Although existing disc prostheses provide advantages over traditional treatment methods, many patients are not candidates for any of these artificial discs due to facet degeneration, instability, poor bone strength, previous surgery, multi-level disease, and pain sources that are non-discogenic. Today patients with these conditions are treated by fusion. However, with some of these conditions it may be possible to use an intervertebral disc instead of fusion if the disc provided less than a full range of motion.

Therefore, a need exists for an improved disc and method for preserving motion and maintaining disc spacing between two vertebrae after removal of an intervertebral disc which provides some limited motion, but less than a full range of motion. Ideally, such improved method and disc would achieve desired stability and maintain spacing between the adjacent vertebrae with a limited range of motion.

BRIEF SUMMARY OF THE INVENTION

Embodiments of the present invention provide a prosthetic intervertebral disc with limited articulation.

In accordance with one aspect of the invention, a prosthetic intervertebral disc includes first and second endplates sized and shaped to fit within an intervertebral space. Each endplate has a vertebral contacting surface and an inner surface. The disc includes a first bearing surface on an inner surface of the first endplate, the first bearing surface comprising a plurality of first steps; and a second bearing surface on an inner surface of the second endplate, the second bearing surface comprising a plurality of second steps mating with the plurality of first steps to provide articulation between the first and second plates.

In accordance with another aspect of the invention, a prosthetic intervertebral disc includes first and second endplates sized and shaped to fit within an intervertebral space. Each endplate has a vertebral contacting surface and an inner surface. The disc includes a first bearing surface on an inner surface of the first endplate, the first bearing surface comprising at least one step; and a second bearing surface. The second bearing surface includes at least one step mating with the at least one step of the first bearing surface to provide articulation between the first and second plates with substantially no rubbing motion between the first and second bearing surfaces.

DETAILED DESCRIPTION OF THE INVENTION

Figure 1:
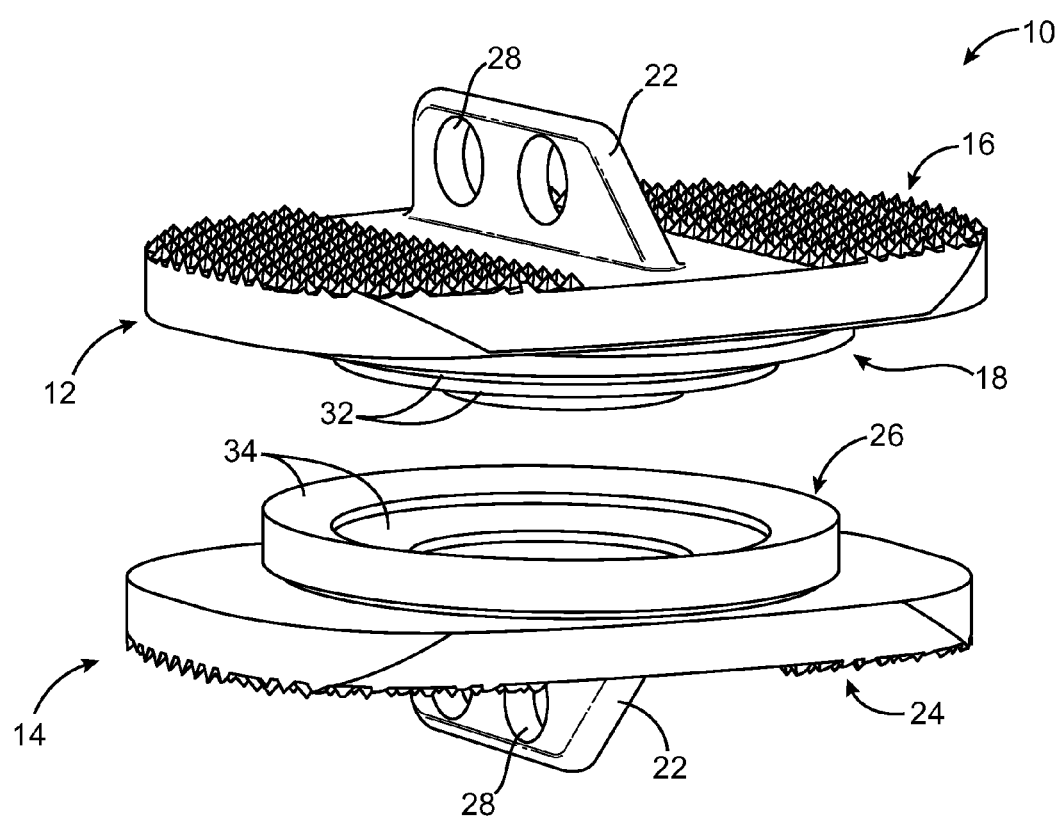
FIG. 1 is an exploded perspective view of a prosthetic intervertebral disc according to one embodiment of the present invention.

A prosthetic intervertebral disc 10 shown in FIG. 1 includes an upper plate 12 and a lower plate 14 and employs congruent stepped features to provide limited motion between the plates. The stepped features can be used to provide articulating motion of a rocking type rather than a rubbing or translating type of motion provided in many artificial discs. The stepped features can be designed to restrict motion in flexion-extension or lateral bending to less than a predetermined angle. The stepped design can be modified to either allow or prevent rotational motion between the plates 12, 14 as will be described in detail below. The limited motion disc, as shown in FIG. 1 substantially prevents translation, however some limited translation can be provided by modification of the relative sizes of the stepped features. For example, the steps can interact to limit translational motion between the plates to less than 1 mm.

The limited motion disc 10 allows the surgeon an alternative to the extremes of no motion provided by fusion procedures and the typical 10-20 degrees of motion in each direction for known articulating discs. The limited motion disc 10 allows the patients that were not previously considered candidates for artificial discs because of instability or other conditions to receive an artificial disc that is more suited to their needs.

In the lumbar spine, the average range of motion is about 8-13 degrees in flexion, about 1-5 degrees in extension, about 1-6 degrees in lateral bending, and about 1-2 degrees in torsion. However, range of motion can vary greatly between patients and some patients could benefit from a disc with more limited motion more like their natural disc. Patients with instability or facet degeneration in particular could benefit from a limited motion disc. The limited motion disc 10 generally provides limited articulation combined with substantially no translation and with or without rotation. This combination of motion can allow many traditional fusion patients to receive an artificial disc and maintain some of their motion.

The rocking motion of the limited motion disc 10 provides a significant advantage over existing discs in the manner in which the moving parts move without rubbing. The rubbing of mating parts in a traditional ball and socket joint articulation creates wear particles as the parts move over one another. In the limited motion disc, the motion between the disc parts is limited by the stepped features to a rocking type motion instead of a rubbing motion. This rocking motion significantly reduces the generation of wear particles. Although the known discs are made out of bio-inert materials and the wear particles are not thought to cause any problems in the majority of patients, the elimination of wear particles would be advantageous in the case of a small as yet unknown minority of patients that may have sensitivity to particles generated over the life of the disc.

Figure 2A:
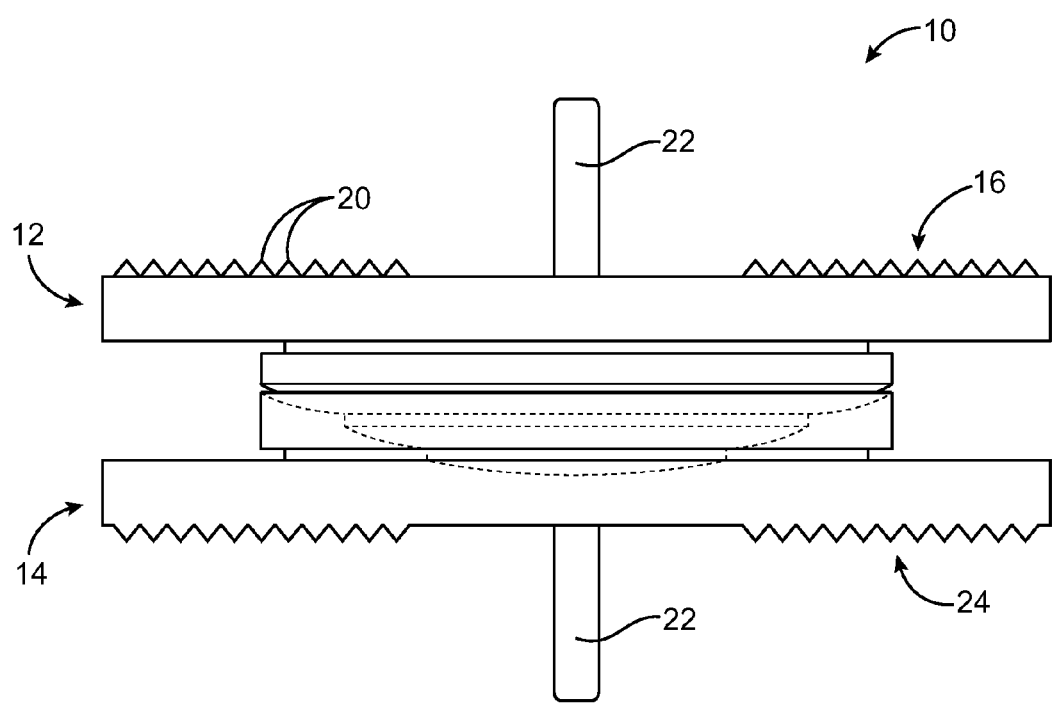
FIG. 2A is a side view of the assembled intervertebral disc of FIG. 1 with the upper and lower plates in vertical alignment.
Figure 2B:
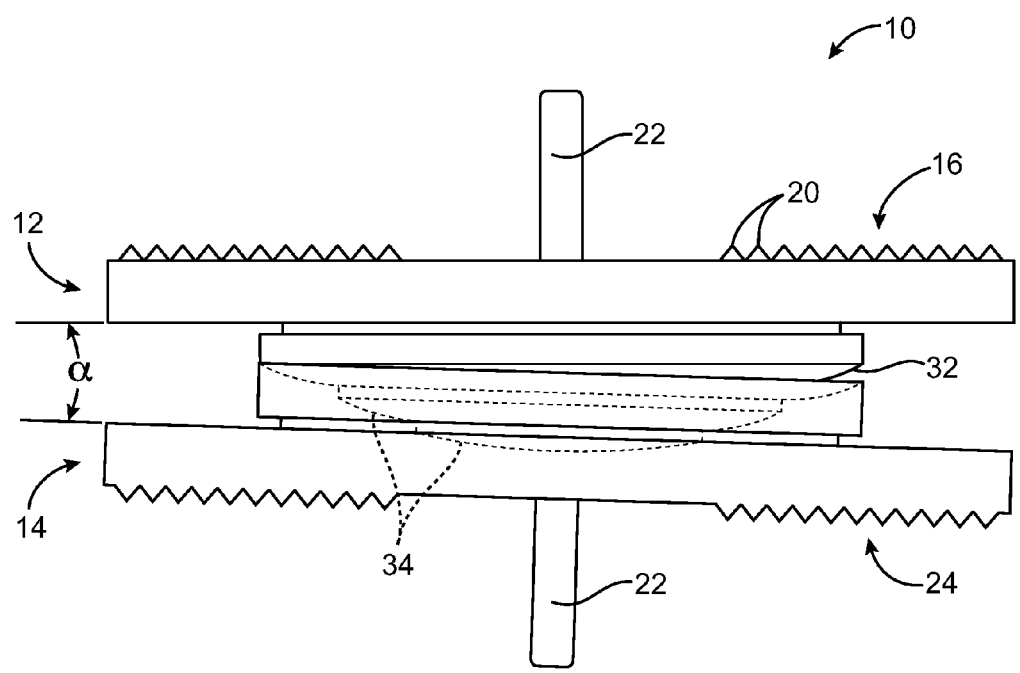
FIG. 2B is a side view of the assembled intervertebral disc of FIG. 1 with the upper and lower plates rotated out of vertical alignment.

Another particular advantage of the stepped bearing surface design of the limited motion disc 10 is the restorative moment exerted by the disc when it is rocked off center. As the plates 12, 14 rotate with respect to one another out of a centered arrangement, a compressive force on the disc 10 provided by the surrounding anatomy of the patient biases the disc toward its neutral, centered and vertically aligned position. FIG. 2A illustrates the disc 10 with the plates 12, 14 in a vertically aligned configuration. FIG. 2B shows the plates 12, 14 at a maximum lateral deflection with an angle α between the plates. This angle α can vary depending on the design and sizing of the cooperating shapes of the bearing surfaces.

The upper plate 12 of FIG. 1 includes an upper vertebral body contacting surface 16 and a lower bearing surface 18. The vertebral body contacting surface 16 in the example of FIG. 1 includes a plurality of serrations 20 and an upstanding central fin 22. The bearing surface 18 includes a plurality of convexly curved steps 32 which together form the bearing surface against which the lower plate 14 articulates.

The lower plate 14 also includes a lower vertebral body contacting surface 24 and an upper bearing surface 26. The bearing surface 26 on the lower plate includes a plurality of concave steps 34. The bearing surfaces 18, 26 together form plurality of cooperating stepped features 32, 34 arranged to allow limited articulation by rocking of the mating stepped surfaces against one another.

Figure 3:
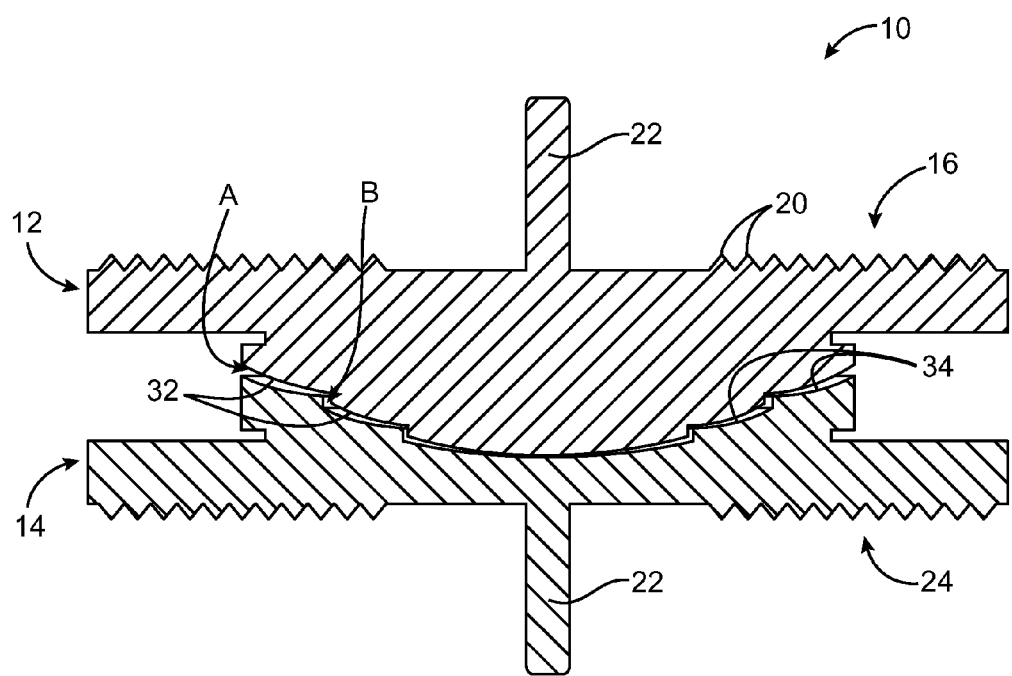
FIG. 3 is a cross sectional view of the intervertebral disc of FIG. 1.

The shapes of the mating bearing surfaces 18, 26 are shown most clearly in the cross sectional view of FIG. 3. The steps 32, 34 limit or substantially prevent translation of the bearing surfaces 18, 26 with respect to one another. In the embodiment shown in FIGS. 1-3, the amount of articulation is determined by the size of the annular gap A between the steps 32, 34 of the upper plate 12 and the lower plate 14. This annular gap A is largest at the outer edges of the bearing surfaces 18, 26 and gets smaller toward a center of the bearing surfaces. The amount of translation between the upper and lower plates 12, 14 is determined by a size of a gap B between the vertical oriented edges of the steps 32, 34. As discussed above, this small gap B significantly reduces the rubbing between bearing surfaces which occurs in a traditional ball and socket joint. Rotation between the upper and lower plates 12, 14 is unlimited in the embodiment of FIGS. 1-3 since the circular shape of the stepped bearing surfaces 18, 26, when viewed in a top view, allow relative rotation of the bearing surfaces. However, other non-circular bearing surfaces can limit or prevent rotation as will be described below.

In the embodiment of FIG. 1, three mating annular stepped surfaces are provided on the upper and lower plates 12, 14. In this example, the steps have the shape of segments of a sphere with a radius of curvature of the convex steps 32 on the upper plate slightly smaller than a radius of curvature of the concave steps 34 on the lower plate 14. In a plan view, the steps 32, 34 of this embodiment are circular allowing unlimited rotational movement between the plates. A height of the space A between the upper and lower bearing surfaces 24, 26 at their outer extremities determines the articulation motion allowed between the plates. In one example, the disc 10 allows motion up to a maximum of about 5 degrees from an initial position in any direction including flexion, extension or either lateral bending direction. In another embodiment, articulation is limited to a maximum of about 3 degrees in any direction. This articulation is about half or less than half of the articulation in the current discs and provides an option for a surgeon of using a disc with improved stability and avoiding fusion. In the embodiments illustrated, the steps each have a width in a substantially radial direction which is at least 3 times a height of the steps in the axial direction. However, other step configurations and number of steps can also be used. Some of these step configurations are discussed below with reference to FIGS. 4 and 5.

The bone integration surfaces 16, 24 of the disc 10 have been shown with serrations 20 and fins 22. However, the outer vertebral body contacting surface 16, 24 may take on any of the configurations known in the art. Oftentimes, the outer surfaces 16, 24 will include one or more surface features and/or materials to enhance attachment of the disc 10 to vertebral bone. For example, the outer surfaces 16, 24 may be machined to have serrations, teeth or other surface features for promoting adhesion of the plates 12, 14 to a vertebra. In the embodiments shown, the serrations 20 are pyramid shaped serrations extending in mutually orthogonal directions, but other geometries of serrations or other features including teeth, grooves, ridges, pins, barbs and combinations thereof would also be useful. When the bone integration structures are ridges, teeth, barbs or similar structures, they may be angled to ease insertion and prevent migration. The outer surfaces may include other fixation means, including one or more fins, pins, or screws. Additionally, the outer surfaces 16, 24 may be provided with a rough microfinish formed by blasting with aluminum oxide microparticles or the like to improve bone integration. In some embodiments, the outer surface 16, 24 may also be titanium plasma spray coated, calcium phosphate coated or HA coated to further enhance attachment of the outer surface to vertebral bone.

The outer bone integration surfaces 16, 24 although shown with one fin 22 extending in an anterior-posterior direction, may also carry more than one fin. The fins 22 are configured to be placed in slots in the vertebral bodies. Preferably, the fins 22 each have a height greater than a width and have a length greater than the height. In one embodiment, the fins 22 are pierced by transverse holes 28 for bone ingrowth. The transverse holes 28 may be formed in any shape and may extend partially or all the way through the fins 22. In alternative embodiments, the fins 22 may be rotated away from the anterior-posterior axis, such as in a lateral-lateral orientation, a posterolateral-anterolateral orientation, or the like to allow the disc 10 to be inserted in any of these directions. In some embodiments, the fins 22 may extend from the outer surfaces 16, 24 at an angle other than 90°. The fins 22 may have any other suitable configuration including various numbers, angles and curvatures, in various embodiments. In some embodiments, the fins 22 may be omitted altogether.

The upper and lower plates 12, 14 may be constructed from any suitable metal, alloy or combination of metals or alloys, such as but not limited to cobalt chrome alloys, titanium (such as grade 5 titanium), titanium based alloys, tantalum, nickel titanium alloys, stainless steel, and/or the like. They may also be formed of ceramics or biologically compatible polymers including PEEK, UHMWPE, PLA or fiber reinforced polymers. However, the vertebral contacting surfaces 16, 24 are preferably formed of a metal with good bone integration properties. The vertebral body contacting surfaces 16, 24 may be coated with the metal for fixation. The plates 12, 14 may be formed of a one piece construction or may be formed of more than one piece, such as different materials coupled together.

Different materials may be used for different parts of the disc 10 to optimize imaging characteristics. Cobalt chrome molybdenum alloys when used for the plates 12, 14 may be treated with aluminum oxide blasting followed by a titanium plasma spray to improve bone integration. PEEK plates may also be coated with titanium plasma spray or provided with titanium screens for improved bone integration. Other materials and coatings can also be used such as titanium coated with titanium nitride, aluminum oxide blasting, HA (hydroxylapatite) coating, micro HA coating, and/or bone integration promoting coatings. Any other suitable metals or combinations of metals may be used as well as ceramic or polymer materials, and combinations thereof. Any suitable technique may be used to couple materials together, such as snap fitting, slip fitting, lamination, interference fitting, use of adhesives, welding and/or the like.

The upper and lower plates 12, 14 can be fabricated from materials which are invisible or near invisible under radiographic imaging, are bio-inert and have high strength such as PEEK. PEEK is part of the family of polyaryletherketones (PAEKs) also called polyketones which have been increasingly employed as implantable materials for orthopedic implants. PAEK is a family of high temperature thermoplastic polymers, consisting of an aromatic backbone molecular chain, interconnected by ketone and ether functional groups. The PAEK family includes poly(aryl-ether-ether-ketone) (PEEK), poly(aryl-ether-ketone-ether-ketone-ketone (PEKEKK), and poly(ether-ketone-ketone) (PEKK) and was originally developed in the aircraft industry for its stability at high temperatures and high strength. Reinforced materials may also be used including PEEK-OPTIMA available from Invibio, Inc., fiber reinforced PEEK, such as PEEK-CFR (carbon fiber reinforced) from Invibio, Inc., glass fiber reinforced PEEK, ceramic filled PEEK, Teflon filled PEEK, barium sulfate filled PEEK or other reinforced or filled materials. As discussed above, materials such as PEEK with poor bone intergration may be provided with a screen or other coating on the bone intergration surfaces of the disc.

Figure 4:
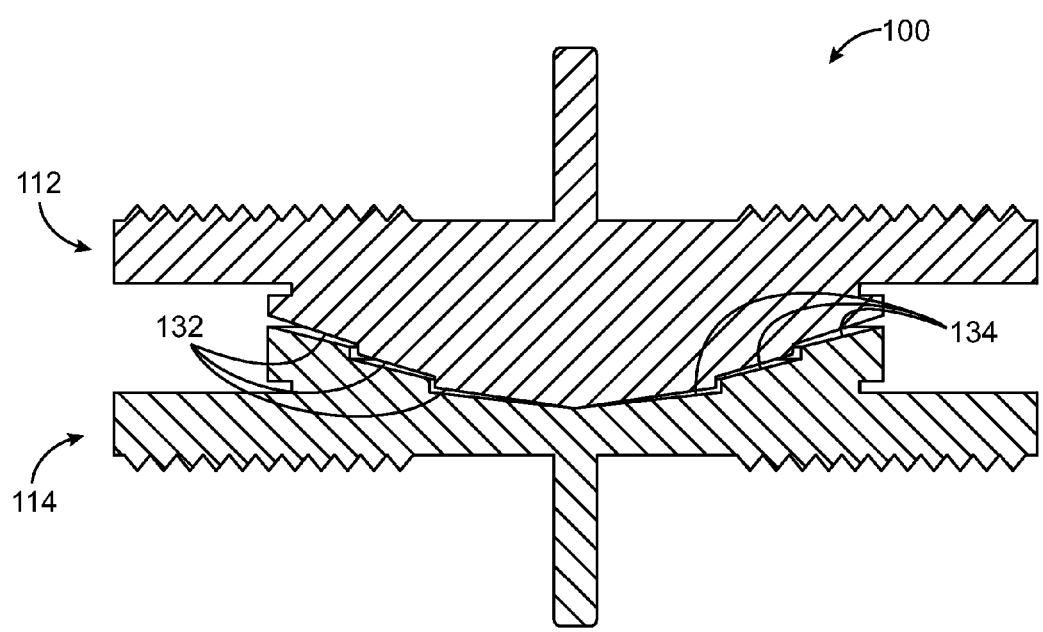
FIG. 4 is a cross sectional view of an alternative embodiment of the intervertebral disc with conical shaped stepped bearing surfaces.

FIG. 4 shows an alternative embodiment of a limited motion disc 100 having conical stepped bearing surfaces. As in the embodiment of FIG. 1, the disc 100 has an upper plate 112 and a lower plate 114. The plates 112, 114 have bearing surfaces with a plurality of steps 132, 134. The steps 132, 134 are in the shape of segments of a cone and in the cross section shown in FIG. 4 each of the stepped surfaces appears flat. The concave/convex shaped steps of FIG. 1 and the conical steps of FIG. 4 are only two examples of the cross sectional shapes of the bearing surfaces which can be used in the present invention. Other shapes may also be used. In another embodiment, different shapes can be used for the upper and lower bearing surfaces, such a planer lower bearing surfaces and convex upper bearing surfaces.

Figure 5:
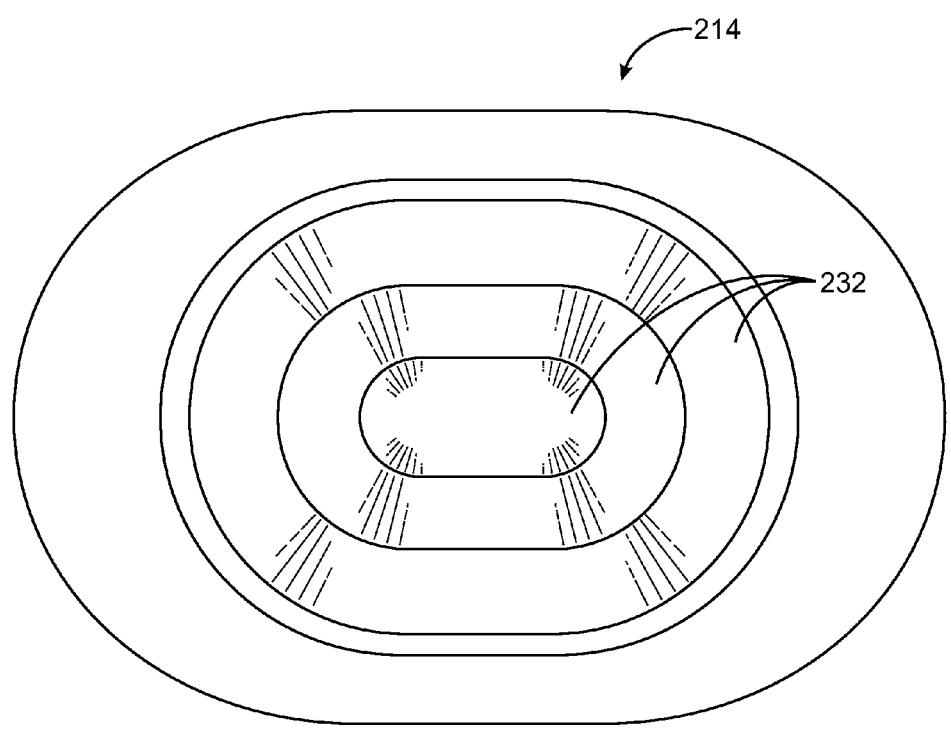
FIG. 5 is a top view of an alternative embodiment of a bottom plate for an intervertebral disc with oval stepped bearing surfaces.

FIG. 5 is a top view of a lower plate 214 of an alternative embodiment of a disc having oval shaped stepped bearing surfaces 232. The oval shape of the stepped bearing surfaces 232 and the cooperating bearing surfaces on the upper plate substantially prevent relative rotation between the plates. An amount of play between the upper and lower bearing surfaces with an oval or other non-circular shaped bearing surface can limit rotation from essentially zero to some small amount of allowable rotation, such as a maximum of about 2 degrees of rotation for a lumbar disc and a maximum of about 5 degrees of rotation for a cervical disc. Other non-circular shaped bearing surfaces can also be used to prevent rotation, such as kidney bean shaped or other irregular shapes. The non-rotatable or limited rotation motion disc is useful in many applications including for patients with degeneration of facets, where further degeneration can be prevention by providing minimal rotation.

In one alternative embodiment of the invention non-symmetrically shaped bearing surfaces are used to tailor the articulation of the disc to the anatomy. In one example, the bearing surfaces are arranged to allow a maximum of 5 degrees of motion in flexion, a maximum of 3 degrees in extension and a maximum of 3 degrees in each direction of lateral bending. This configuration is useful particularly in the lumbar spine where the average range of motion of the various segments is larger in flexion that in extension or lateral bending. For the cervical spine, the range of motion varies depending on the spine level, but generally range of motion in lateral bending is larger than motion in flexion and extension. In one example for the cervical spine, the bearing surfaces are arranged to allow a maximum of 5 degrees of motion in flexion and extension and a maximum of 7 degrees in each direction of lateral bending.

Figure 6:
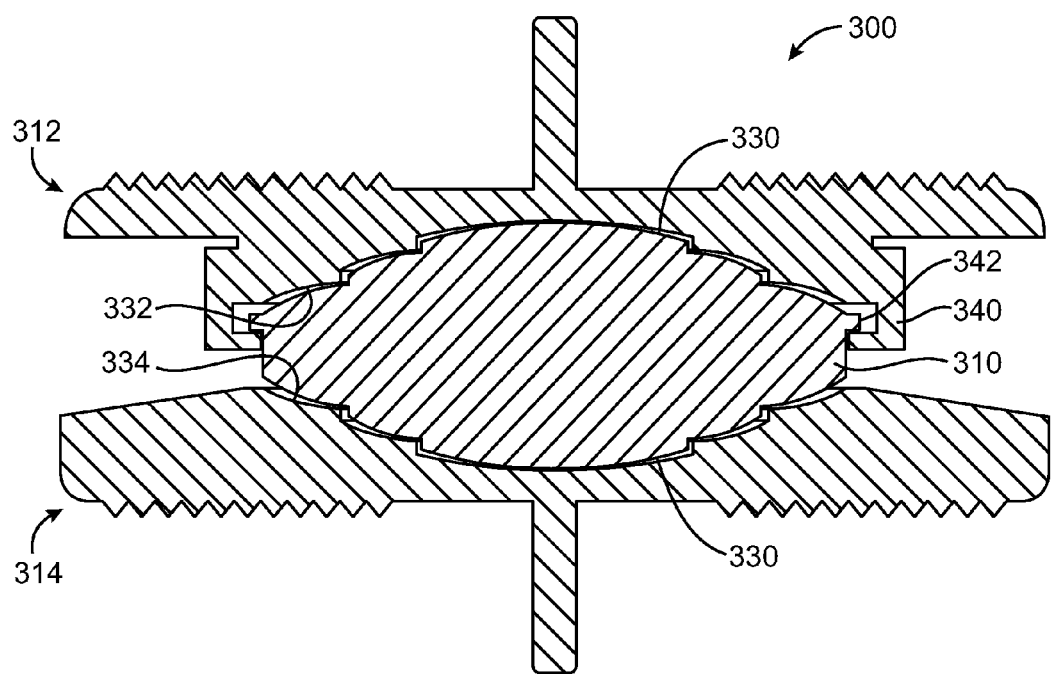
FIG. 6 is a side cross sectional view of an alternative embodiment of the intervertebral disc with a mobile core design.

FIG. 6 illustrates an alternative embodiment of a three piece limited motion disc 300. The three piece disc 300 has upper and lower plates 312, 314 and a mobile core 310. The plates 312, 314 have inner stepped bearing surfaces 332, 334 which cooperate with corresponding upper and lower stepped bearing surfaces 330 on the core. The core 310 can be held in position between the pates 312, 314 by a retaining feature such as a retaining ring 340 which accommodates an annular ring 342 on the core. The mobile core disc 300 can provide somewhat more motion in translation and articulation than the two piece ball and socket type disc of FIG. 1 using similarly shaped bearing surfaces. The three piece disc 300 provides the same advantages as the two piece disc by limiting the amount of rubbing motion between moving parts and the associated generation of wear particles.

Although the core 310 of FIG. 6 has been shown as circular in cross section with spherically shaped bearing surfaces steps 330, other shapes may be used including oval, elliptical, or kidney bean shaped. These non-circular shaped cores can be used to limit rotational motion between the upper and lower plates 312, 314. When the core 330 is formed of a polymer such as PEEK which is invisible under radiographic imaging, it may be desirable to have a radiographic marker imbedded within the core.

In an alternative embodiment of the mobile core disc of FIG. 6, the core may have different upper and lower bearing surfaces. For example, the upper bearing surface of the core may have the concentric step configuration as shown while the lower bearing surface of the core may have a cylindrical, flat, or spherical shaped surface and a correspondingly shaped mating surface on the lower plate.

Any of the embodiments disclosed herein may be provided with a rotation limiter. The rotation limiter may be in the form of the shape of the steps, as in the embodiment of FIG. 5. Alternatively, the rotation limiter may be in the form of a tab on one of the steps o a first bearing surface and a corresponding slot on a corresponding step of the second bearing surface.

In use, any of the intervertebral discs described herein are surgically implanted between adjacent spinal vertebrae in place of a damaged disc. Those skilled in the art will understand the procedure of preparing the disc space and implanting the disc which is summarized herein. In a typical artificial disc procedure, the damaged disc is partially or totally removed and the adjacent vertebrae are forcibly separated from one another or distracted to provide the necessary space for insertion of the disc. One or more slots are cut into the vertebrae to accommodate the fins, if any. The plates are slipped into place between the vertebrae with their fins entering the slots cut in the opposing vertebral surfaces to receive them. The plates may be inserted simultaneously or sequentially and with or without the core, if any. After partial insertion of the disc, the individual plates can be further advanced independently or together to a final position. Once the disc has been inserted, the vertebra move together to hold the assembled disc in place. The vertebral contacting surfaces of the plates including the serrations and the fins locate against the opposing vertebrae and, with passage of time, firm connection between the plates and the vertebrae will be achieved as bone tissue grows over the serrated finish and through and around the fin.

The motion limiting stepped bearing surfaces described herein can be used with many artificial disc designs and with different approaches to the intervertebral disc space including anterior, lateral, posterior and posterior lateral approaches. Although various embodiments of such an artificial disc are shown in the figures and described further herein, the general principles of these embodiments, namely providing a stepped bearing surface design which limits articulation, translation and/or rotational motion, may be applied to any of a number of other disc prostheses designs.

While the exemplary embodiments have been described in some detail, by way of example and for clarity of understanding, those of skill in the art will recognize that a variety of modifications, adaptations, and changes may be employed. Hence, the scope of the present invention should be limited solely by the appended claims.

What is claimed is:

1. A prosthetic intervertebral disc comprising:
first and second endplates sized and shaped to fit within an intervertebral space, each endplate having a vertebral contacting surface and an inner surface, wherein a first longitudinal axis and a second longitudinal axis extends between the vertebral contacting surface and the inner surface of the first and second endplates, respectively;
a first continuous bearing surface on the inner surface of the first endplate, the first continuous bearing surface comprising a plurality of concentric first steps arranged in a concave configuration, wherein an end of the first longitudinal axis extends to the first continuous bearing surface;
a second continuous bearing surface on the inner surface of the second endplate, the second continuous bearing surface comprising a plurality of concentric second steps arranged in a convex configuration, wherein each step of the plurality of concentric second steps is complementary to, and mates with a corresponding step of the plurality of first steps in the concave configuration to provide articulation between the first and second endplates, wherein an end of the second longitudinal axis extends to the second continuous bearing surface,
wherein each of the plurality of first steps and second steps has a rise and a run,
wherein the plurality of first steps and the plurality of second steps mate so that the end the first longitudinal axis and the end of the second longitudinal axis are retained substantially adjacent to each other so as to define a pivot point about which the first and second endplates are adapted to rock relative to each other, and
wherein each step of the plurality of concentric first steps has an annular periphery disposed fully about the first longitudinal axis and each step of the plurality of concentric second steps has an annular periphery disposed fully about the second longitudinal axis.

2. The disc of claim 1, wherein the annular peripheries of the first steps and second steps are circular.

3. The disc of claim 1, wherein the annular peripheries of the first steps and second steps are oval.

4. The disc of claim 1, wherein the first steps and second steps each have a curved cross sectional profile.

5. The disc of claim 1, wherein the first steps and second steps each have a planar cross sectional profile.

6. The disc of claim 1, wherein the first steps have a planar cross sectional profile and the second steps have a curved cross sectional profile.

7. The disc of claim 1, wherein the first and second steps each have a width in a radial direction at least 3 times a height of the steps in an axial direction.

8. The disc of claim 1, wherein the plurality of first steps comprise at least three steps.

9. The disc of claim 1, wherein the first steps and the second steps interact to limit articulating motion between the plates to a maximum of 5 degrees in the anterior, posterior, or lateral directions.

10. The disc of claim 1, wherein the first steps and the second steps interact to limit rotational motion between the plates to a maximum of 2 degrees.

11. The disc of claim 1, wherein the first steps and the second steps interact to limit translational motion between the plates to less than 1 mm.

12. The disc of claim 1, further comprising at least one fin extending from each of the vertebral contacting surfaces.

13. The disc of claim 1, wherein the first steps and second steps are arranged in strata.

14. A prosthetic intervertebral disc comprising:
   first and second endplates sized and shaped to fit within an intervertebral space, each endplate having a vertebral contacting surface and an inner surface, wherein a first longitudinal axis and a second longitudinal axis extends between the vertebral contacting surface and the inner surface of the first and second endplates, respectively;
   a first continuous bearing surface on the inner surface of the first endplate, the first continuous bearing surface comprising a plurality of first steps formed on a unitary piece of the first endplate, the plurality of first steps arranged in a concave configuration, wherein an end of the first longitudinal axis extends to the first continuous bearing surface;
   a second continuous bearing surface, the second continuous bearing surface comprising a plurality of second steps formed on a unitary piece of the second endplate, the plurality of second steps arranged in a convex configuration, wherein each step of the plurality of second steps is complementary to a corresponding step of the plurality of first steps in the concave configuration, wherein an end of the second longitudinal axis extends to the second continuous bearing surface,
   wherein the plurality of first steps and the plurality of second steps mate so that the end the first longitudinal axis and the end of the second longitudinal axis are retained substantially adjacent to each other so as to define a pivot point about which the first and second endplates are adapted to rock relative to each other,
   wherein each of the plurality of first steps and second steps has a rise and a run,
   and wherein each step of the plurality of concentric first steps has an annular periphery disposed fully about the first longitudinal axis and each step of the plurality of concentric second steps has an annular periphery disposed fully about the second longitudinal axis.

* * * * *